(12) United States Patent
Lu

(10) Patent No.: US 9,943,079 B2
(45) Date of Patent: Apr. 17, 2018

(54) MODIFIED MINERAL-BASED FILLERS

(75) Inventor: Jie Lu, Lompoc, CA (US)

(73) Assignee: Imerys Filtration Minerals, Inc., San Jose, CA (US)

(*) Notice: Subject to any disclaimer, the term of this patent is extended or adjusted under 35 U.S.C. 154(b) by 125 days.

(21) Appl. No.: 12/740,474

(22) PCT Filed: Oct. 27, 2008

(86) PCT No.: PCT/US2008/081263
§ 371 (c)(1),
(2), (4) Date: Apr. 29, 2010

(87) PCT Pub. No.: WO2009/058707
PCT Pub. Date: May 7, 2009

(65) Prior Publication Data
US 2010/0260866 A1   Oct. 14, 2010

Related U.S. Application Data

(60) Provisional application No. 60/983,935, filed on Oct. 30, 2007.

(51) Int. Cl.
*A01N 25/08*  (2006.01)
*A01N 59/16*  (2006.01)

(52) U.S. Cl.
CPC .................................. *A01N 25/08* (2013.01)

(58) Field of Classification Search
None
See application file for complete search history.

(56) References Cited

U.S. PATENT DOCUMENTS 2,066,271 A   12/1936   Irwin
2,504,404 A    4/1950   Flenner
(Continued)

FOREIGN PATENT DOCUMENTS

CN   1186712 A    7/1998
CN   1318675 A   10/2001
(Continued)

OTHER PUBLICATIONS

Gibbard J., Public Health Aspects of the Treatment of Water and Beverages with Silver, Amer J Public Health, Feb. 1937, 112-119.*
(Continued)

*Primary Examiner* — Robert A Wax
*Assistant Examiner* — Thor Nielsen
(74) *Attorney, Agent, or Firm* — Finnegan, Henderson, Farabow, Garrett & Dunner LLP

(57) ABSTRACT

Modified mineral-based fillers with enhanced retention of at least one active ingredient and/or enhanced antimicrobial capabilities are described. The materials comprise at least one mineral-based filler subjected to at least one modification process, which may be either a cationic modification process, a surface adsorption process, a surface retention process, or a combination thereof, with at least one active ingredient, followed by at least one thermal treatment. The at least one active ingredient may be a metal substance or other biocide, fungicide, mildewcide, antibiotic, insecticide, preservative, or antimicrobial agent. Methods for enhancing the antimicrobial activity of products in applications such as polymers, clothing, surgical equipment, coatings, and paints are also described.

4 Claims, 8 Drawing Sheets

(56) References Cited

U.S. PATENT DOCUMENTS

| | | | |
|---|---|---|---|
| 2,595,290 | A | 5/1952 | Quinn |
| 3,151,993 | A | 10/1964 | Bundy |
| 4,092,245 | A | 5/1978 | Franks et al. |
| 4,255,341 | A | 3/1981 | Solomon |
| 4,407,865 | A | 10/1983 | Nice |
| 4,505,889 | A | 3/1985 | Amick |
| 4,552,591 | A | 11/1985 | Millar |
| 4,579,779 | A | 4/1986 | Ohno |
| 4,656,057 | A | 4/1987 | Amick |
| 4,849,223 | A | 7/1989 | Pratt et al. |
| 4,906,466 | A | 3/1990 | Edwards et al. |
| 4,911,898 | A | 3/1990 | Hagiwara et al. |
| 5,180,585 | A | 1/1993 | Jacobson et al. |
| 5,229,124 | A | 7/1993 | Rei et al. |
| 5,413,788 | A | 5/1995 | Edwards et al. |
| 5,478,563 | A | 12/1995 | Erami |
| 5,648,086 | A | 7/1997 | Redlich et al. |
| 6,051,246 | A * | 4/2000 | Shiau et al. ............ 424/409 |
| 6,102,994 | A | 8/2000 | Zhou et al. |
| 6,139,313 | A | 10/2000 | Kostuch et al. |
| 6,362,449 | B1 | 3/2002 | Hadidi et al. |
| 6,444,726 | B1 | 9/2002 | Brunt et al. |
| 6,905,698 | B1 | 6/2005 | Aldcroft et al. |
| 6,911,898 | B2 | 6/2005 | Chung |
| 7,381,675 | B1 * | 6/2008 | Ruszkay ............ B01J 21/08 502/60 |
| 2004/0229034 | A1 | 11/2004 | Djokic |
| 2005/0211635 | A1 * | 9/2005 | Yeh .................. A01N 59/16 210/732 |
| 2006/0024381 | A1 * | 2/2006 | Schwartz et al. ........ 424/641 |
| 2006/0035097 | A1 | 2/2006 | Batdorf |
| 2006/0108262 | A1 | 5/2006 | Takatsu et al. |
| 2006/0180552 | A1 | 8/2006 | Downs |
| 2006/0188580 | A1 * | 8/2006 | Sacks .................. A01N 25/12 424/489 |
| 2006/0246149 | A1 | 11/2006 | Buchholz et al. |
| 2007/0031515 | A1 | 2/2007 | Stucky et al. |
| 2007/0060691 | A1 | 3/2007 | Kim |
| 2007/0202318 | A1 * | 8/2007 | Smith et al. ............ 428/323 |
| 2008/0277116 | A1 * | 11/2008 | Roddy et al. ............ 166/292 |
| 2008/0305027 | A1 * | 12/2008 | Johnston et al. ........ 423/339 |
| 2009/0214606 | A1 * | 8/2009 | Bujard .................. A01N 25/08 424/401 |
| 2010/0119461 | A1 * | 5/2010 | Bicard-Benhamou . A01N 59/16 424/49 |
| 2010/0239679 | A1 * | 9/2010 | Greene .................. A01N 25/26 424/490 |

FOREIGN PATENT DOCUMENTS

| | | | |
|---|---|---|---|
| DE | 1417969 A1 | 3/1960 | |
| EP | 0 602 810 A1 | 6/1994 | |
| EP | 0 736 249 A1 | 10/1996 | |
| GB | 306547 | 2/1928 | |
| GB | 1 590 573 | 6/1981 | |
| GB | 2 235 462 A | 3/1991 | |
| JP | 2-215704 | 8/1990 | |
| JP | 2001-10902 | 1/2001 | |
| WO | WO 2006078176 A1 * | 7/2006 | |
| WO | WO-2006/120135 A1 | 11/2006 | |
| WO | WO-2006120135 A1 * | 11/2006 | ............ A01N 25/08 |
| WO | WO 2009/058707 A1 | 5/2009 | |

OTHER PUBLICATIONS

Merck Index, O'Neil, ed., 14$^{th}$ edition, 2006, morphine entry No. 06276.*
Merck Index, O'Neil, ed., 14th edition, 2006, sodium entry 08570.*
Merck Index, O'Neil, ed., 14th edition, 2006, copper entry No. 02519.*
Merck Index, O'Neil, ed., 14th edition, 2006, Vitamin A entry No. 10013.*
"NRC urges minimal Beryllium Exposure" in Chem. Eng. News 86(33): 26 (2008), Abstract.*
http://www.5novels.com/ScienceFiction/Asimov19/17494.html, downloaded on Jun. 17, 2015.*
Super Floss Diatomaceous Earth MSDS [downloaded on Feb. 19, 2016 from the website http://www.matweb.com/search/datasheet.aspx?matguid=ac8de1d89e064ce3aba6d456385aca45&ckck=1].*
Super Floss Diatomaceous Earth MSDS.*
Breese, Kevin D., "Killer Fillers: Fillers with Antimicrobial Effects", Conference for High Performance Fillers, Mar. 2007, Hamburg, Germany, pp. 1-8.
Masuda, Noriaki; Kawashita, Masakazu; and Kokubo, Tadashi, "Antibacterial Activity of Silver-Doped Silica Glass Microspheres Prepared by a Sol-Gel Method", Journal of Biomedical Materials Research Part B; Applied Biomaterials 83B(1), 2007, pp. 114-120.
International Search Report and Written Opinion from International Application No. PCT/US2008/081263 filed Oct. 27, 2008.
Office Action dated Jul. 20, 2012, for related Chinese Application No. 200880124160.X.

* cited by examiner

MODIFIED MINERAL-BASED FILLERS

This application is a U.S. national stage entry under 35 U.S.C. § 371 from PCT International Application No.PCT/US2008/081263, filed Oct. 27, 2008, and claims priority to and the benefit of the filing date of U.S. Provisional Application No. 60/989,935, filed Oct. 30, 2007, the subject matter of both of which are incorporated herein by reference.

FIELD OF THE INVENTION

This application and the inventions described herein generally discuss and relate to modified mineral-based fillers with enhanced antimicrobial capabilities.

BACKGROUND OF THE INVENTION

Using active ingredients such as metals and other biocides to prevent microbial contamination is an essential concern in daily life, in everywhere from, for example, surface areas in bathrooms, to surgical instruments, to wall paints. U.S. Pat. No. 6,905,698 B1, which is incorporated by reference herein in its entirety, generally discusses certain methods by which biocides can be used. Incorporating active ingredients into mineral-based fillers can ideally enhance antimicrobial capabilities of the finished products while additionally fulfilling, and without compromising, other filler functions. However, the effectiveness of the antimicrobial capabilities may decrease over time as the active ingredients leach out of the mineral-based fillers.

This invention generally relates to modified mineral-based fillers that can be incorporated into resins to produce a range of products, such as paints, clothing, polymers, surgical equipment, and coatings. Introducing active ingredients such as biocides into or with carrier materials has generally been disclosed for at least some variety of applications, such as in U.S. Pat. No. 5,648,086, in U.S. Patent Application Publication No. 2006/0035097, and in the use of celite as a biocide carrier. Introducing active ingredients such as metals into or with carrier materials has also generally been disclosed for at least some variety of applications, such as in U.S. Pat. Nos. 4,407,865 and 4,505,889, U.S. Patent Application Publication Nos. 2006/0180552 A1 and 2006/0246149 A1, in Japanese Patent Application Nos. 02215704 A2 and 2001010902 A2, as well as in Kevin D. Breese, *Killer Fillers: Fillers with Antimicrobial Effects*, 3d Int'l Conference for High Performance Fillers (Mar. 14-15, 2007).

Historically, however, active ingredients in mineral-based fillers leach out of the fillers during the life of the product in which they are incorporated, limiting the antimicrobial capabilities of the products, both in their initial antimicrobial capability and their continued antimicrobial capability as the active ingredient may diffuse from the mineral-based fillers. Current practices attempt to prolong the antimicrobial capabilities of different materials by slowing the diffusivity of the active ingredients in various ways. U.S. Pat. No. 5,180,585 and U.S. Patent Application No. 2006/0246149 A1 generally discusses a protective surface coating; U.S. Patent No. 6,905,698 B1 also generally discusses a protective surface coating or surface cleaning compositions; U.S. Pat. No. 4,656,057 attempts to solve the problem through use of porous or perforated membranes; EP-A-0602810, EP-A-0736249, GB-A-2235462 and GB-A-1590573 and U.S. Pat. No. 5,229,124 attempts to control the release of biocide to inhibit bacterial and fungal growth using sol gel chemistry to entrap the biocide but allow release thereof by diffusion from the hydrogel network; U.S. Pat. No. 4,579,779 involves encapsulation of organic liquids such as perfumes, food flavors, pesticides, and fungicides by combining liquid and silica in such a way that droplets of the organic liquid are encompassed within a shell of silica particles. U.S. Pat. No. 4,552,591 describes a composition intended to protect polymer dispersions used in oil field water treatment. Finally, modification of mineral-based fillers may have been generally disclosed, such as in U.S. Pat. Nos. 2,066,271 and 6,911,898. Doping materials for enhanced antimicrobial activity for plastics does not use mineral-based fillers, see, e.g., Masuda et al., *Antimicrobial Activity of Silver-Doped Silica Glass Microspheres Prepared by Sol-Gel Method*, J. BIOMED. MATER. RES. B. APPL. BIOMATER. 83B(1), 114-20 (2007). Indeed, none of those references appear to contemplate at least the modification of the mineral-based fillers, followed by thermal treatment such as calcination, as a method to enhance antimicrobial capabilities of the mineral-based fillers.

SUMMARY OF THE INVENTION

Figure 1:
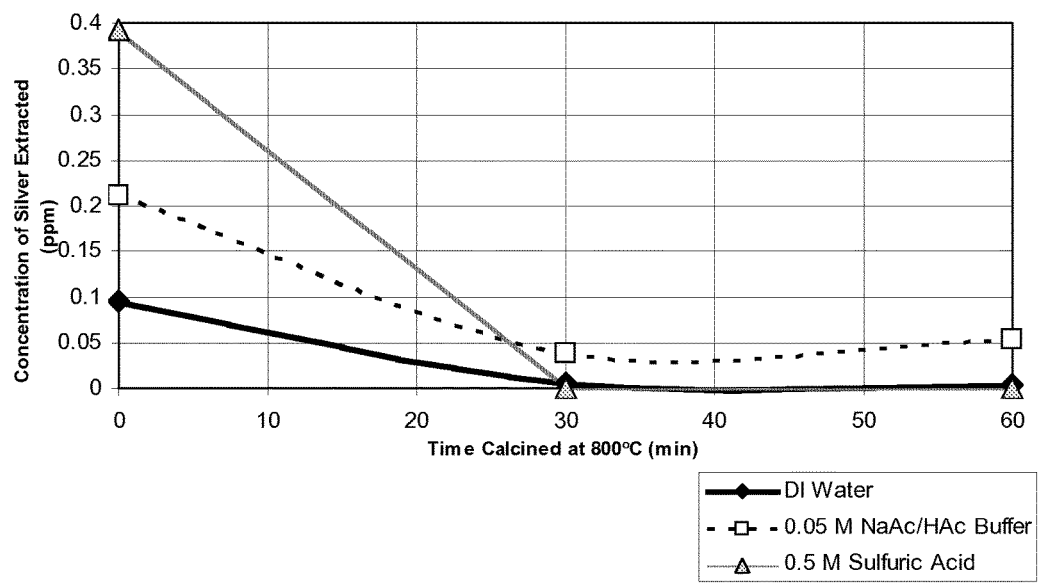
FIG. 1 is a diagram illustrating the migration of silver from calcined 50 ppm silver-doped filler in three different solutions: DI water, 0.05 M NaAc/Hac buffer, and 0.5 M sulfuric acid.
Figure 2:
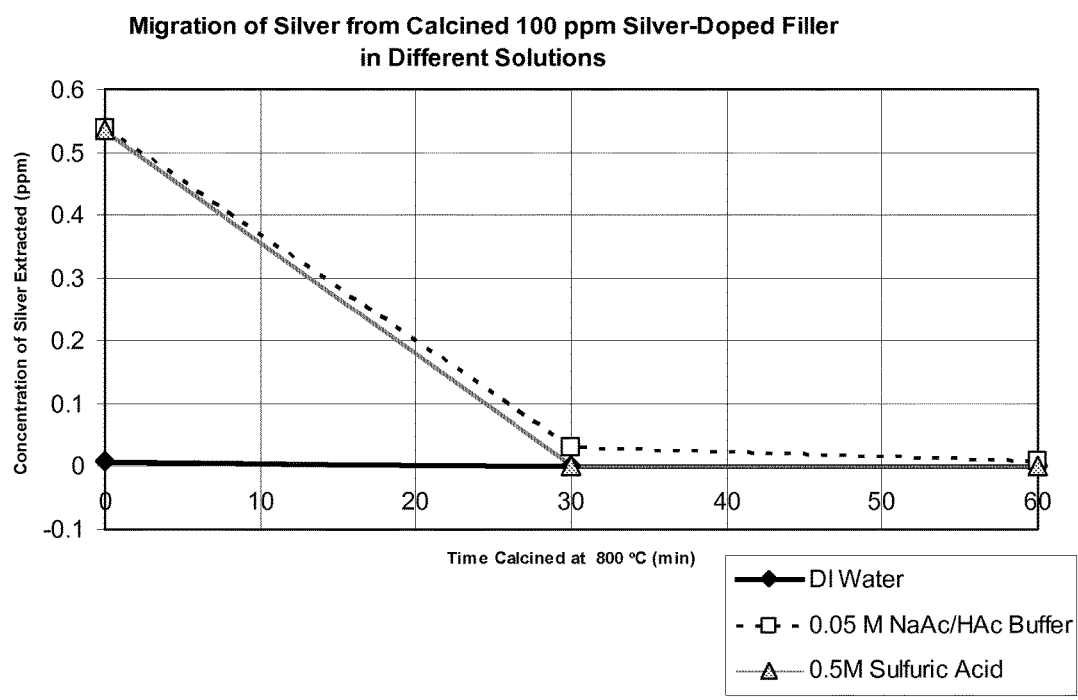
FIG. 2 is a diagram illustrating the migration of silver from calcined 100 ppm silver-doped filler in three different solutions: DI water, 0.05 M NaAc/Hac buffer, and 0.5 M sulfuric acid.
Figure 3:
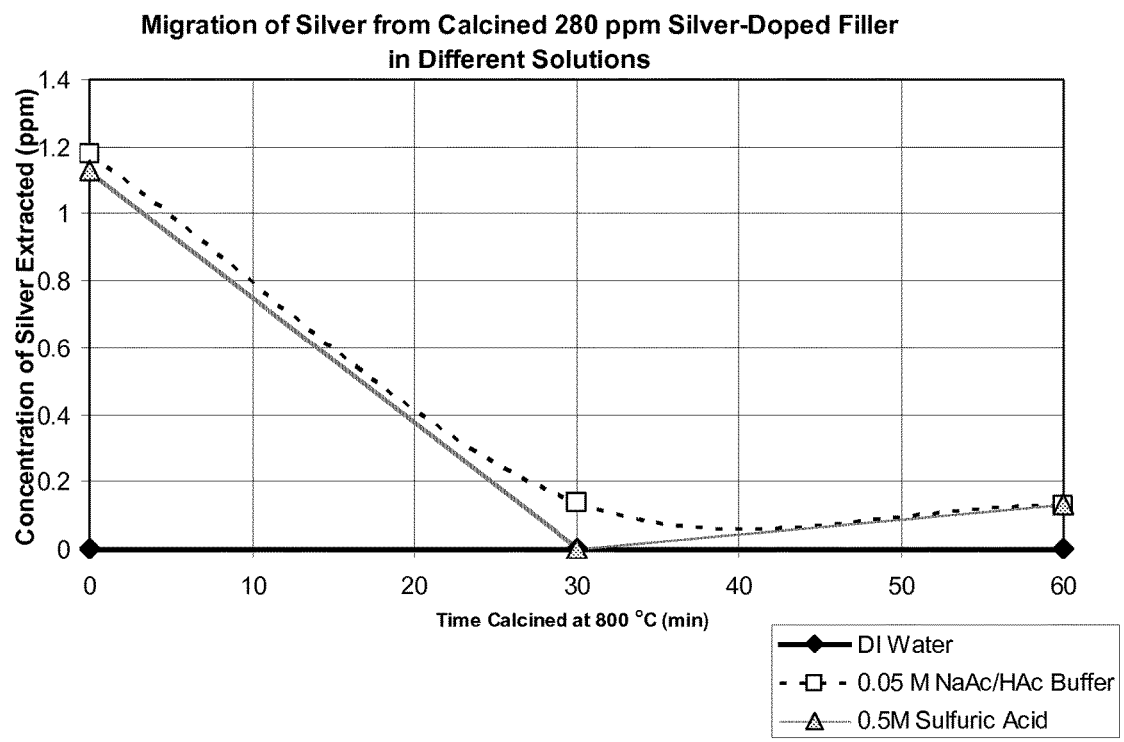
FIG. 3 is a diagram illustrating the migration of silver from calcined 280 ppm silver-doped filler in three different solutions: DI water, 0.05 M NaAc/Hac buffer, and 0.5 M sulfuric acid.
Figure 4:
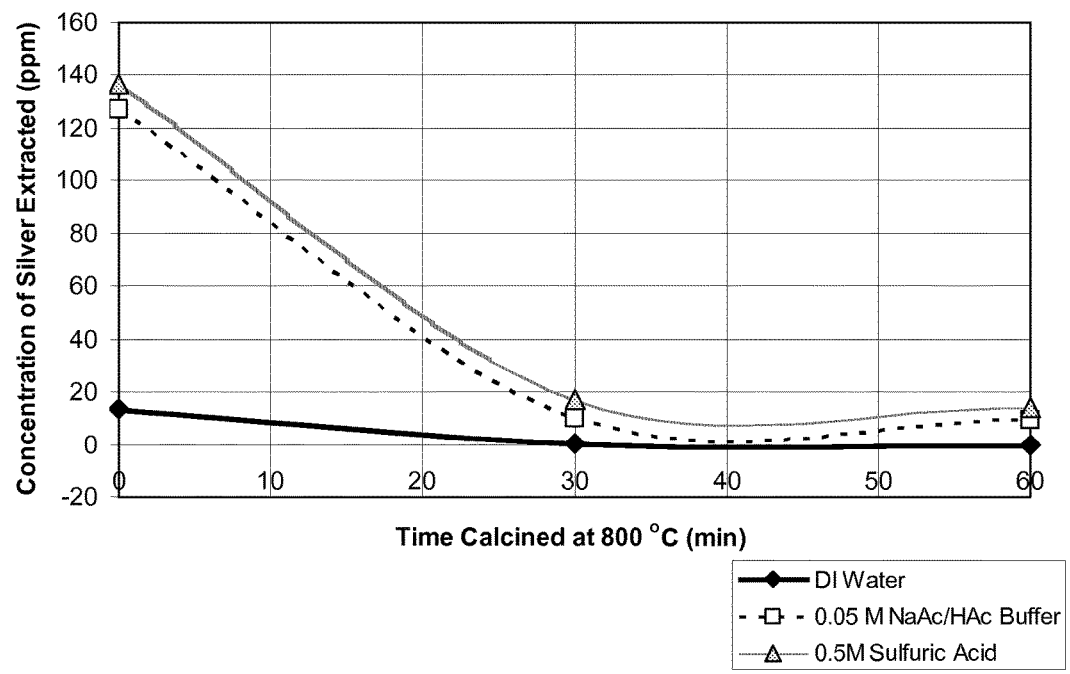
FIG. 4 is a diagram illustrating the migration of silver from calcined 2.55% silver-doped filler in different solutions: DI water, 0.05 M NaAc/Hac buffer, and 0.5 M sulfuric acid.
Figure 5:
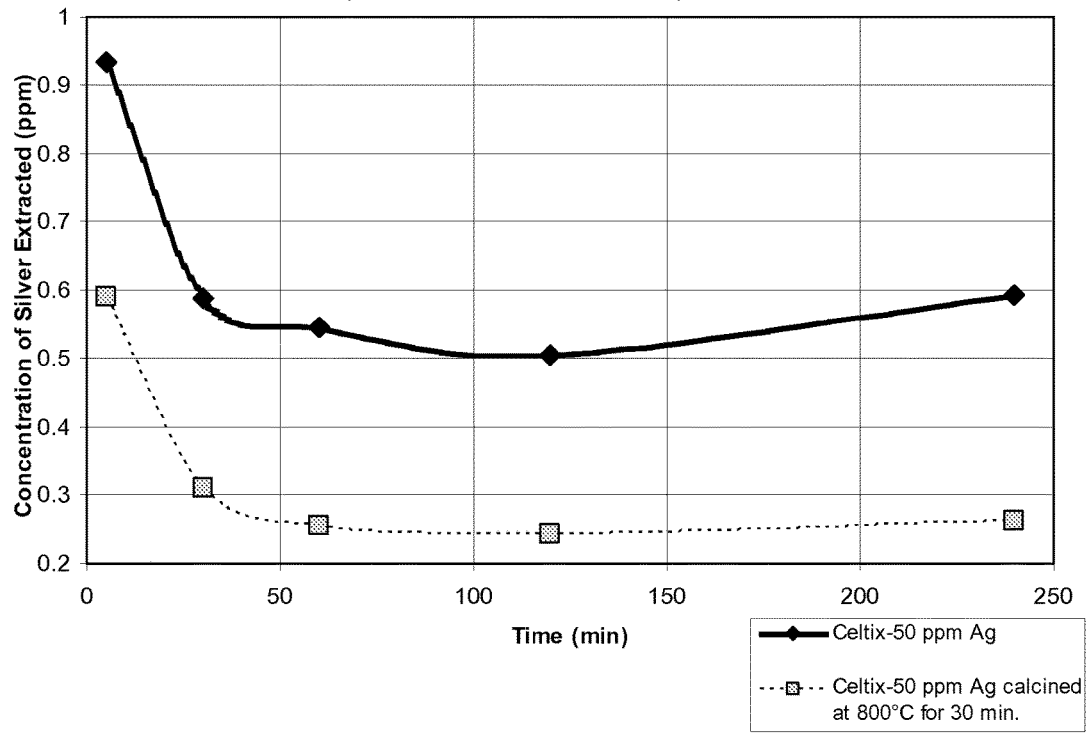
FIG. 5 is a diagram illustrating the extraction of 50 ppm Ag-doped fillers with 0.5 M sulfuric acid.
Figure 6:
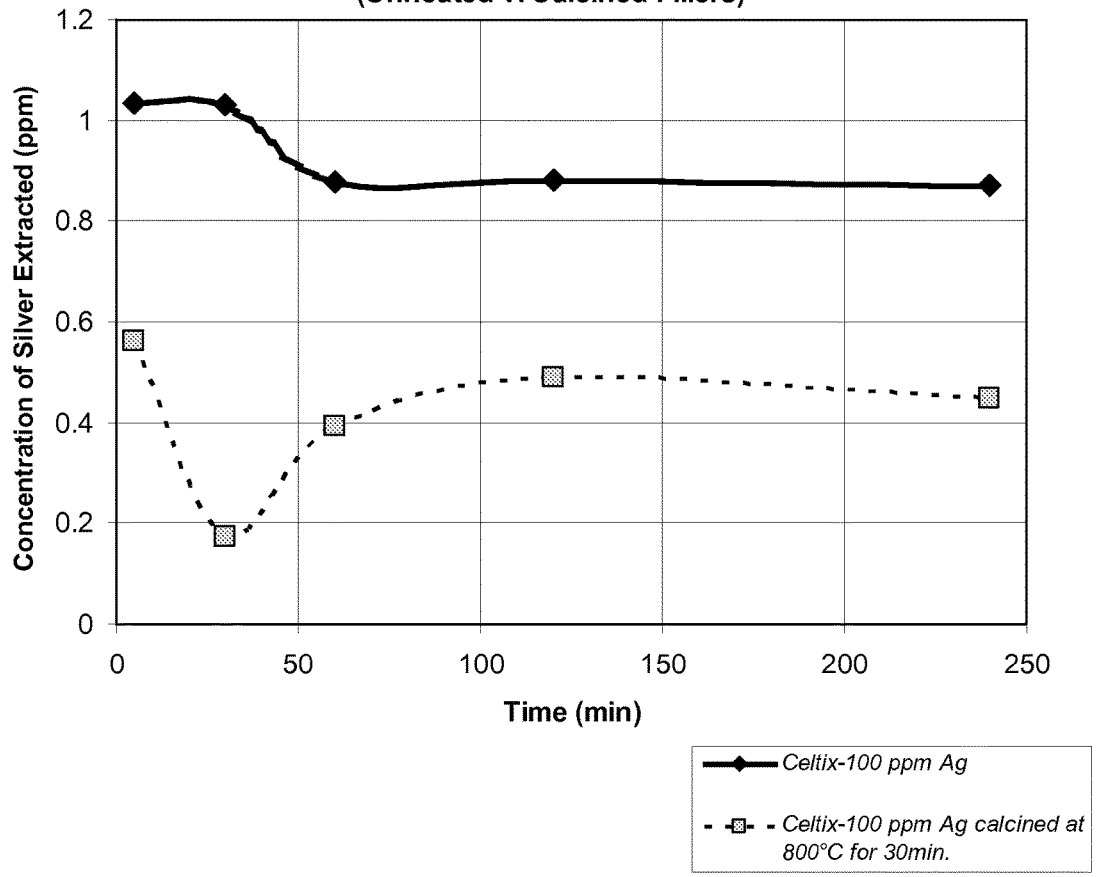
FIG. 6 is a diagram illustrating the extraction of 100 ppm Ag-doped fillers with 0.5 M sulfuric acid.
Figure 7:
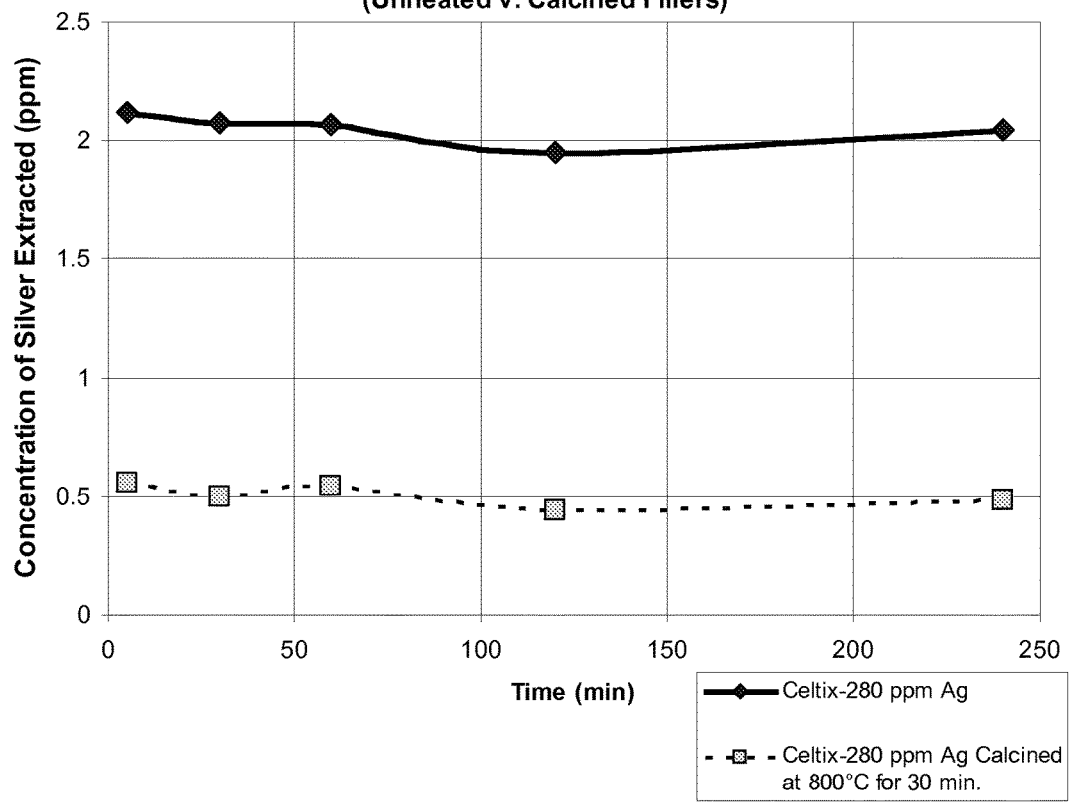
FIG. 7 is a diagram illustrating the extraction of 280 ppm Ag-doped fillers with 0.5 M sulfuric acid.
Figure 8:
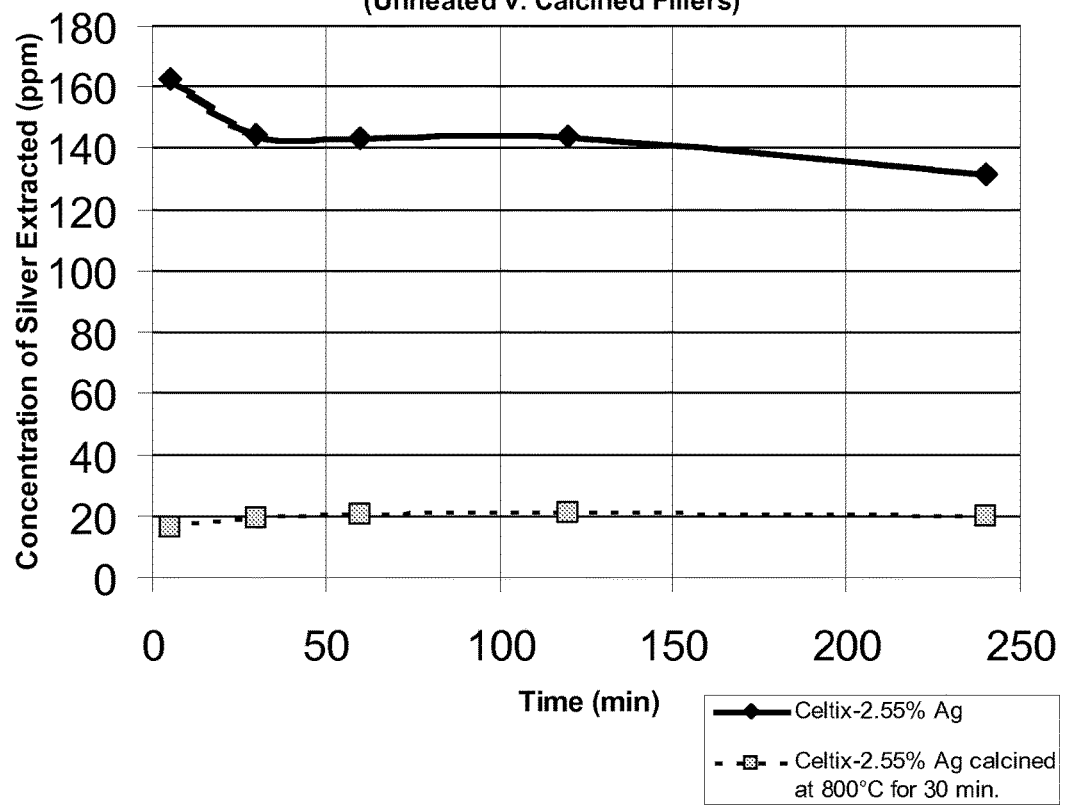
FIG. 8 is a diagram illustrating the extraction of 2.55% Ag-doped fillers with 0.5 M sulfuric acid.

Disclosed generally herein are modified mineral-based fillers with enhanced antimicrobial capabilities. Also disclosed generally herein are methods for producing products with enhanced antimicrobial capabilities, such as biocidal polymers, clothing, surgical equipment, coatings, and paints. The method generally comprises decreasing the migration rate of at least one active ingredient (e.g., metal and/or other biocide) from the product through at least one modification process, which may comprise subjecting at least one mineral-based filler to at least one active ingredient, followed by at least one thermal treatment. Methods for using the modified mineral-based fillers with enhanced antimicrobial capabilities are also disclosed.

DETAILED DESCRIPTION OF THE INVENTION

At least one mineral-based filler undergoes at least one modification process comprising subjecting the at least one mineral-based filler to at least one active ingredient, which may be adsorbed or retained onto the surface, and/or may cationically modify the surface, of the at least one mineral-based filler, followed by at least one thermal treatment. In one embodiment, the at least one modification and/or the at least one thermal treatment allow for decreased migration of the at least one active ingredient from the at least one mineral-based filler, thereby enhancing the antimicrobial capability of the at least one mineral-based filler.

Mineral-Based Filler

The modified mineral-based fillers disclosed herein comprise at least one mineral-based filler. Combinations of functional mineral-based fillers may be used. The skilled artisan will readily understand appropriate mineral-based fillers for use in the inventions described herein. In one embodiment, the at least one mineral-based filler is any mineral-based substrate whose surface is capable of retaining at least one active ingredient and/or being modified through an at least one modification process and/or at least one thermal treatment. In another embodiment, the at least one mineral-based filler is any mineral-based substrate that, after surface adsorption/retention and/or cationic modification, may experience reduced leaching of at least one active ingredient. In a further embodiment, the mineral-based filler is a natural mineral-based filler. In yet another embodiment, the mineral-based filler is a synthetic mineral-based filler.

In one embodiment, the at least one mineral-based filler is calcium silicate. In one embodiment, the calcium silicate is derived from diatomaceous earth. In another embodiment, the calcium silicate is derived from limestone. In another embodiment, the mineral-based filler is diatomaceous earth. Diatomaceous earth is, in general, a sedimentary biogenic silica deposit comprising the fossilized skeletons of diatoms, one-celled algae-like plants that accumulate in marine or fresh water environments. Honeycomb silica structures generally give diatomaceous earth useful characteristics such as absorptive capacity and surface area, chemical stability, and low bulk density. In one embodiment, diatomaceous earth comprises about 90% $SiO_2$ mixed with other substances. In another embodiment, diatomaceous earth comprises about 90% $SiO_2$, plus various metal oxides, such as but not limited to Al, Fe, Ca, and Mg oxides. In one embodiment, the diatomaceous earth is natural, e.g., unprocessed. The impurities in natural diatomaceous earth, such as clays and organic matters, may provide higher cation exchange capacity. In another embodiment, the diatomaceous earth is calcined. In a further embodiment, the diatomaceous earth is flux calcined. In yet another embodiment, diatomaceous earth is a commercially available super-fine diatomaceous earth product, such as but not limited to Superfloss® available from Celite Corporation. In yet a further embodiment, the diatomaceous earth is CelTiX™, available from World Minerals Inc.

In another embodiment, the at least one mineral-based filler is perlite. Perlite, in general, identifies any naturally occurring siliceous volcanic rock that can be expanded with heat treatment. In one embodiment, perlite comprises between about 70% and about 74% silica, about 14% alumina, between about 2% and 6% water, and trace impurities. In one embodiment, the perlite is ore. In another embodiment, the perlite is expanded. In a further embodiment, the perlite is a fine perlite. In yet another embodiment, the perlite is Harborlite® 635, a very fine grade of perlite available from Harborlite Corp., a subsidiary of World Minerals Inc.

In a further embodiment, the at least one mineral-based filler is at least one clay. In one embodiment, the at least one clay is smectite, which may also be referred to as bentonite clay. Bentonite clay generally comprises absorbent aluminum phyllosilicates, impure clays, and may consist mostly of montmorillonite, $(Na,Ca)_{0.33}(Al,Mg)_2Si_4O_{10}(OH)_2 \cdot (H_2O)_n$, which may also be referred to as Fuller's earth. In another embodiment, the at least one clay is illite clay. Exemplary illite clays include, but are not limited to, gumbelite, hydromica, hydromuscovite, muscovite, and sericite. In a further embodiment, the at least one mineral-based filler comprises diatomaceous earth derived calcium silicate and at least one clay.

In a further embodiment, the at least one mineral-based filler is kaolin clay, which may also be referred to as china clay or hydrous kaolin. In one embodiment, kaolin clay comprises predominantly mineral kaolinite $(Al_2Si_2O_5(OH)_4)$, anhydrous aluminum silicate, and amounts of various impurities. The kaolin clay may be used in any one of various common forms. Exemplary forms of kaolin clays include, but are not limited to, airfloat kaolin clay, water-washed kaolin clay, delaminated kaolin clay, and calcined kaolin clay.

In yet another embodiment, the at least one mineral based filler is a metallic oxide. In still a further embodiment, the at least one multi-functional filler is a synthetic calcium silicate hydrate $(CaSiO_3)$. An exemplary synthetic $CaSiO_3$ is Micro-Cel® E, available from Advanced Minerals Corp., a subsidiary of World Minerals Inc. In another embodiment, the at least one mineral-based filler is vermiculite. In further embodiment, the at least one mineral-based filler is a phyllosilicate.

In one embodiment, the at least one mineral-based filler is talc. Talc may be used in any of various common forms. In one embodiment, the talc comprises greater than about 90% $Mg_3Si_4O_{10}(OH)_2$ (magnesium silicate hydroxide) and accessory minerals in varying amounts, including, but not limited to, chlorite, serpentine, quartz, tremolite, anthophyllite, and carbonates such as magnesite, dolomite, and calcite. In another embodiment, the talc is platy talc. In a further embodiment, the talc is industrial talc. In yet another embodiment, the talc is tremolitic talc. In still a further embodiment, the at least one multi-functional filler is a synthetic magnesium silicate hydrate $(MgSiO_3)$. An exemplary synthetic $MgSiO_3$ is Celkate® T21, available from Advanced Minerals Corp., a subsidiary of World Minerals Inc.

In one embodiment, the at least one mineral-based filler is mica. Mica may be used in any of various common forms. In one embodiment, the mica of the general Formula (I):

$$X_2Y_{4-6}Z_8O_{20}(OH,F)_4 \qquad (I)$$

wherein X may be, but is not limited to, K, Na, Ca, Ba, Rb, or Cs; Y may be, but is not limited to, Al, Mg, Fe, Mn, Cr, Ti, and Li; and, Z may be, but is not limited to, Si, Al, Fe, and Ti.

In another embodiment, the at least one mineral-based filler is selected from the group consisting of, but not limited to, activated carbon, high aspect ratio Wollastonite, low aspect ratio Wollastonite, amorphous silicas, amorphous aluminas, alumina trihydrate, barite (barium sulfate), bentonite, ground calcium carbonate, precipitated calcium carbonate, calcium sulfate, gypsum, carbon black, clay, chlorite, dolomite, feldspar, graphite, huntite, hydromagnesite, hydrotacite, magnesia, magnesite (magnesium carbonate), magnesium hydroxide, magnetite $(Fe_3O_4)$, nepheline syenite, olivine, pseudoboehmites (forms of microcrystalline aluminum hydroxide), pyrophyllite, titania, titanium dioxide (e.g., rutile), Turkish powder, stone powder, pumice, coral sand, natural and synthetic zeolites, and zinc oxide, all of which may be used in any of various common forms.

In another embodiment, the at least one mineral-based filler is silica. Silica may be used in any of various common forms. Examples of silica forms include, but are not limited to, ground silica, novoculite silica, precipitated silica, fumed silica, and fumed amorphous silica. In one embodiment, the silica is synthetic silica. Examples of synthetic silicas include, but are not limited to, silica gels, silica colloids, synthetic fused silica, and doped synthetic fused silica. In another embodiment, the silica is an aluminosilicate with the basic structural composition $AlSiO_4$. Exemplary aluminosilicates include, but are not limited to, calcium aluminosilicate, sodium aluminosilicate, potassium aluminosilicate, zeolite, and kyanite. In a further embodiment, the mineral-based filler is not glass. In yet another embodiment, the mineral-based filler is not silica glass. In yet a further embodiment, the mineral-based filler is not silica glass microspheres.

In yet another embodiment, the at least one mineral-based filler is a mineral powder. Exemplary mineral powders include, but are not limited to, fly ash, low calcium fly ash, Class F fly ash, Class C fly ash, bark ash, bottom ash, pet coke ash, silica fume, condensed silica fume, rice hull ash, slag, air-cooled slag, normal weight slag, lightweight slag, expanded slag, pelletized slag, ground granulated blast furnace slag, sandy volcanic ash, volcanic tuffs, and natural pozzolans.

In one embodiment, the average diameter of the particles of the at least one mineral-based filler is less than about 20 microns. In another embodiment, the average diameter of the particles of the at least one mineral-based filler is less than about 10 microns. In yet another embodiment, the average diameter of the particles of the at least one mineral-based filler is less than about 5 microns. In still another embodiment, the average diameter of the particles of the at least one mineral-based filler is between about 1 and about 10 microns. In another embodiment, the average diameter of the particles of the at least one mineral-based filler is between about 1 and about 20 microns. In yet another embodiment, the average diameter of the particles of the at least one mineral-based filler is between about 1 and about 5 microns.

Active Ingredient

The at least one mineral-based filler is subjected to at least one modification process with at least one active ingredient. The at least one active ingredient may take any of various forms and fulfill any of various functions. In one embodiment, the at least one active ingredient is any substance that may exchange ions with the at least one mineral-based filler. In another embodiment, the at least one active ingredient is any substance that will bind to, be adsorbed by, be retained by, or otherwise interact with the at least one mineral-based filler.

In one embodiment, the at least one active ingredient is chosen from the group consisting of a metal, metal oxide, or salt thereof. Examples of the at least one active ingredient include, but are not limited to, silver oxides, silver silicates (e.g., silver metasiliate ($Ag_2SiO_3$) and silver orthosilicate ($Ag_4SiO_4$)), silver salts (e.g., silver halogenide, silver nitrate, silver sulfate, silver carboxylates (e.g., silver acetate, silver benzoate, silver carbonate, silver citrate, silver lactate, and silver salicylate)), Hydrogen Peroxide/Silver (such as Accepta 8102 available from Accepta™ Advanced Chemical Technologies), copper oxides, copper salts (e.g., copper sulfide, copper nitrate, copper carbonate, copper sulfate, copper halogenides, and copper carboxylates), zinc oxides, and zinc salts (e.g., zinc sulfide, zinc silicate, zinc acetate, zinc chloride, zinc nitrate, zinc sulfate, zinc gulconate, zinc lactate, zinc oxalate, zinc iodate, and zinc iodide).

In another embodiment, the at least one active ingredient is a biocidal metal ion. Exemplary biocidal metal ions include, but are not limited to, silver, copper, magnesium, aluminum, niobium, silicon, tantalum, zirconium, cobalt, hafnium, lanthanum, tungsten, calcium, titanium, vanadium, cerium, strontium, tin, and zinc ions. In one embodiment, the at least one active ingredient is a substance that produces a biocidal metal ion when used in the processes or final products described herein. In another embodiment, the at least one active ingredient is a substance that comprises a biocidal metal ion.

In a further embodiment, the at least one active ingredient is a biocide. Exemplary classes of biocides include, but are not limited to, germicides, bactericides, fungicides, algaeicides, rodenticides, avicides, molluscicides, piscicides, insecticides, acaricides and products to control other arthropods, disinfectants, human hygiene biocidal products, private area and public health disinfectants, veterinary hygiene biocidal products, food and feed area disinfectants, drinking water disinfectants, pest repellants, pest attractants, antifouling products, embalming fluids, taxidermist fluids, and vertebrate control biocides. Exemplary biocides include, but are not limited to, Silver acetate, Silver carbonate, Silver chloride, Silver copper zeolite, Silver fluoride, Silver iodide, colloidal Silver nitrate, Silver orthophosphate ($Ag_3PO_4$), Silver oxide ($Ag_4O_4$), Silver salt of partially polymerized mannuronic acid, Silver sodium hydrogen zirconium phosphate ($Ag_{0.18}Na_{0.57}H_{0.25}Zr_2(PO_4)_3$), Silver thiocyanate, Silver thiuronium acrylate co-polymer, Silver zeolite, Silver zinc zeolite, Silver, Silver Borosilicate, Silver Magnesium Aluminium Phosphate Zinc 8-quinolinolate, Zinc bacitracin, Zinc chloride, Zinc dehydroabietylammonium 2-ethylhexanoate, Zinc dodecyl benzene sulphonate, Zinc silicate, Zinc sulfate heptahydrate, Zinc sulfate, Zinc Nitrate and anhydrous Zinc trichlorophenate Ziram.

In another embodiment, the at least one active ingredient is chosen an inorganic biocide. Exemplary inorganic biocides include, but are not limited to, cuprous oxide, and inorgano-silver.

Combinations of modification processes and active ingredients are contemplated. In one embodiment, the at least one mineral-based filler is subjected to at least one modification process with at least two active ingredients. In such an embodiment, the first active ingredient may be a biocide and the second active ingredient may be chosen from the group consisting of a metal, metal oxide, and salt thereof. In another such embodiment, the first active ingredient may be a biocide and the second active ingredient may be a biocidal metal ion. In another embodiment, the at least one mineral-based filler is subjected to at least two modification processes. In such an embodiment, the first modification process comprises subjecting the at least one mineral-based filler to at least one active ingredient, and the second modification process comprises the modified mineral-based filler from the first modification process to either the same or to a different at least one active ingredient. In a further embodiment, the at least one mineral-based filler is subjected to a modification process comprising at least one active ingredient chosen from the group consisting of a metal, metal oxide, salt thereof, and biocidal metal ion, followed by a second modification process comprising at least one active ingredient chosen from a biocide.

Modification Process

The modification process of a filler may be carried out by cation exchange of the at least one active ingredient with the mineral-based filler and/or by surface adsorption/retention of the at least one active ingredient. The at least one mineral-based filler is subjected to at least one modification process comprising at least one active ingredient. In one embodiment, the modification process is any process that changes or modifies the ionic composition of the mineral-based filler, such as a cationic modification. In another embodiment, the modification process is any process that affixes or otherwise bonds at least one active ingredient to the at least one mineral-based filler. In a further embodiment, the modification process is surface adsorption. In yet another embodiment, the modification process is surface retention.

In one embodiment, the modification process is cationic modification. In one embodiment, the cationic modification process is ion-exchange. In another embodiment, the cationic modification process is characterized in that an organic polymer or mixture of organic polymers containing the at least one mineral-based filler is moulded and then treated with at least one aqueous solution of at least one water-soluble salt and at least one active ingredient, to exchange at least part of the ions of at least one mineral-based filler with at least part of the ions of the at least one active ingredient. In another embodiment, the at least one cationic modification process is characterized in that the at least one mineral-based filler retains the ions of the at least one active ingredient at ion-exchangeable sites of the at least one mineral-based filler in an amount less than the ion-exchange saturation capacity of the mineral-based filler. In a further embodiment, at least a portion of the ion-exchange process of the at least one cationic modification process occurs whereby ions of the at least one active ingredient are converted into, for example, oxides, hydroxides, or basic salts, and then the ions of the at least one active ingredient deposit into the microspores and/or onto the surface of the at least one mineral-based filler.

In one embodiment, the mineral-based filler of this invention retains biocidal metal ions in an amount from about 0.001% to 10% by weight of the mineral-based filler. In another embodiment, the mineral-based filler retains biocidal metal ions in ion-exchanged form at an amount as high as about 100% of the theoretical ion-exchange capacity of the at least one mineral-based filler. In another embodiment, the ion-exchanged mineral-based filler has a relatively low degree of ion-exchange, prepared by performing the ion-exchange using a metal ion solution having a concentration less than about 0.5 M. In another such embodiment, the concentration of the solution is less than about 0.01 M.

In another embodiment, the at least one cationic modification process adds the at least one active ingredient and the at least one mineral-based filler to an organic polymer or a mixture of polymers. In a further embodiment, the at least one cationic modification process exchanges ions between silver and diatomaceous earth (as an at least one mineral-based filler), whereby an aqueous solution of a water-soluble silver salt (such as silver nitrate) is used for surface adsorption and/or retention, or to cationically modify the at least one mineral-based filler by ion-exchange with silver ions.

The amount of the at least one active ingredient incorporated with the at least one mineral-based filler as a result of an at least one cationic modification process will vary according to the active ingredient, filler, and modification process chosen. In one embodiment, the amount of the at least one active ingredient incorporated with the at least one mineral-based filler is less than about 35% by weight of the final product. In another embodiment, the amount is about 0.001 to about 15% by weight. In a further embodiment, the amount is about 0.001 to about 5% by weight. In yet another embodiment, the amount is about 50 ppm. In yet a further embodiment, the amount is about 100 ppm. In still another embodiment, the amount is about 280 ppm. In still a further embodiment, the amount is about 2.55% by weight.

Cation exchange of at least one ionic, metallic active ingredient with the at least one mineral-based filler may be performed by dissolving the metallic ion compound in aqueous solution, followed by mixing with the at least one mineral-based filler powders. In one embodiment, the slurry formed by the filler and the biocide solution is filtered after about 5 minutes to about 4 hours of soaking or mixing, depending on the equilibrium time. The collected filler can then be thermally treated to affix the exchanged biocide ions in the structures of the filler phases. The filtrant can be saved for use in subsequent ion exchange treatment. In another embodiment, the metallic biocide solution that contains the at lease one active ingredient is mixed with the at least one mineral-based filler, the slurry is then dried and homogenized before further thermal treatment by calcination. In yet another embodiment, the cationic modification causes or allows for surface adsorption. In another embodiment, the cationic modification causes or allows for surface retention. In a further embodiment, the cationic modification causes or allows for surface adsorption and surface retention.

Thermal Treatment

The thermal treatment is carried out so that the at least one active ingredient incorporated by at least one modification can be affixed or "locked" on the at least one mineral-based filler.

After the at least one mineral-based filler is subjected to the at least one modification process with the at least one active ingredient, the filler is then subjected to at least one thermal treatment. In one embodiment, the modified mineral-based filler is subjected to at least one thermal treatment so that no measurable crystalline silica is formed. In another embodiment, the modified mineral-based filler is subjected to at least one thermal treatment to effect a phase transformation, including, but not limited to, surface sintering, partial melting decomposition, conversion, glomerization, devitrification, or any combination thereof. In a further embodiment, the at least one thermal treatment changes the structure of the modified mineral-based filler into that of a crystalline solid.

The selection of the at least one thermal treatment may vary according to the choice of the at least one mineral-based filler, the at least one active ingredient, the at least one modification process, and the desired end product. Appropriate thermal treatment processes are well-known to the skilled artisan, and include those now known or that may hereinafter be discovered.

In one embodiment, the at least one thermal treatment is any treatment that "locks" the at least one active ingredient into or onto the filler such that they become integrated parts of the at least one filler material. In another embodiment, the at least one thermal treatment comprises calcination. In one such embodiment, calcination is carried out at temperatures below the melting point of the materials that comprise the modified mineral-based filler. In another such embodiment, calcination is carried out at or above the thermal decomposition temperature of the modified mineral-based filler and may cause decomposition and/or volatization reactions. In a further such embodiment, calcination is carried out at or above the transition temperature of the modified mineral-based filler and may cause a phase transition. In yet another such embodiment, calcination is carried out at temperatures ranging from about 600° C. to about 900° C. In yet a further such embodiment, calcination is carried out at temperatures ranging from about 800° C. to about 1200° C.

Calcination may be carried out in any vessel capable of thermally treating the modified mineral-based filler. In one embodiment, calcination is carried out in furnace. In another embodiment, calcination is carried out in a reactor. In a further embodiment, calcination is carried out in a kiln. In yet another embodiment, calcination is carried out in a rotary kiln. In yet a further embodiment, calcination is carried out in a shaft furnace. In still another embodiment, calcination is carried out in a multiple hearth furnace. In still a further embodiment, calcination is carried out in a fluidized bed reactor.

In another embodiment, the at least one thermal treatment comprises roasting. In one such embodiment, the modified mineral-based filler is first dried in a single stage dryer, and then the dried modified mineral-based filler may be sent to a waste separator to remove any wet end waste. The modified mineral-based filler may then be roasted in a suitable vessel or series of vessels at a temperature ranging from about 850 to about 1600° F. The at least one roasting vessel may be chosen from a group including, but not limited to, pre-heaters, flash heaters, flash calciners, flash roasting reactors, and toroidal bed reactors. Examples of such vessels include, but are not limited to, flash calciners available from FFE Minerals, and the TORBED reactor available from Torftech Ltd. and discussed, for example, in U.S. Pat. No. 6,139,313. The vessel may be equipped with at least one means for heating the diatomaceous earth feed, for instance direct heating mechanisms such as internal hot air or gas flow, and indirect heating mechanisms utilizing external heat sources in combination with any heat transfer surface conventionally used in the art. In one embodiment, the at least one roasting vessel may be heated at least in part by a counter-current gas flow originating from another step in the process, for instance a subsequent calcination step or another process in the treatment plant.

In one embodiment, the feed may be roasted at a temperature ranging from about 850° F. to about 1600° F. (i.e., about 427° C. to about 871° C.). In another embodiment, the feed may be roasted at a temperature ranging from about 900° F. to about 1000° F. (i.e., about 482° C. to about 538° C.). In a further embodiment, the feed may be roasted at a temperature ranging from about 1200° F. to about 1292° F. (i.e., about 649° C. to about 700° C.). In one embodiment, the retention time may be less than about 4 minutes. In another embodiment, the retention time is from about 2 to about 3 minutes. In a further embodiment, the retention time is from about 2 to about 10 seconds.

Other examples of appropriate at least one thermal treatments may be used. In one embodiment, the at least one thermal treatment is microwave heating. In another embodiment, the at least one thermal treatment is microwave plasma heating. In a further embodiment, the microwave plasma heating involves the generation of two large-amplitude coherent electron cyclotron waves in the plasma.

Microorganisms

Modified mineral-based fillers according to the present invention may exhibit increased levels of at least one antimicrobial activity. In one embodiment, the at least one antimicrobial activity is a bacteriostatic effect, e.g., preventing the growth of new microorganisms. In another embodiment, the at least one antimicrobial activity is a biocidal effect, e.g., reducing a given concentration of microorganisms. In a further embodiment, the at least one antimicrobial activity is a sterilizing effect, e.g., reducing or killing substantially all of a given collection of microorganisms. The at least one antimicrobial activity may be effective against one or more microorganisms.

The microorganisms may be any of those now known to the skilled artisan or hereafter discovered that may experience at least one antimicrobial activity in response to the at least one active ingredient of the cationically modified, mineral-based fillers of the present invention. Exemplary microorganisms include, but are not limited to, bacteria (e.g., gram positive and gram negative bacteria), yeasts, fungi, mildew, viruses, and combinations thereof. Further exemplary microorganisms include, but are not limited to, *Staphylococci, Micrococci, Escherichia, Escherichia coli, Pseudomonas, Pseudomonas aeruginosa, Pseudomonas vescicularis, Stenotrophomonas maltophilia* (previously known as *Xantomonas maltophilia*), *Klebsiella pneumoniae* ATC 13315, *S. Aureus* NCTC 10788, *S edidermis* biotype 3, *Lactobacillus buchneri, PS aeruginosa* NCTC 6749, *Serratia marcescens* NCTC 1377, *Listeria monocytogenes* NCTC 10357, *B subtilis* NCTC 3160, *B cereus* NCTC 7464, *C albicans* NCYC 597, *C albicans* NCPF 3179, *C parapsilosis, C bordinii, Sacc cerevisae* NCYC 200, *Sacc rouxii* NCYC 381, pink yeast, odium sp, *Aspergillus flavus, Aspergillus fumigatus* IMI 134735, *Aspergillus niger* IMI 17454, *Aspergillus glaugus, Penicillium notatum, Cladosporium herbarum, Trichothecium ciride, acternaria alternate, Myrothecium verruccaria, Verticillium psalliotae, Bacilli, Salmonella, Shigella, Porphyromonas, Prevotella, Wolinella, Campylabacter, Propionibacterium, Streptococci, Cprumebacterium, Treponema, Fusobacterium, Bifidobacterium, Lactobacillus, Actinomyces, Candida, Malazessia*, and *Aspergillus*. The skilled artisan readily understands that the embodiments disclosed herein may effectively destroy or inhibit the growth of any microorganism, depending upon the at least one active ingredient used in the modified mineral-based filler.

Uses for Modified Mineral-Based Fillers

At least one modified mineral-based filler disclosed herein may be used in any application now known to the skilled artisan or hereafter discovered, in which enhanced performance of the application is desired though increased retention of the at least one active ingredient and/or increased levels of at least one antimicrobial activity. Exemplary applications include, but are not limited to, animal feed, cosmetic formulations, paints, inks, home care products, animal care products, building materials, paper products, fabric products (e.g., textiles), products for personal and work hygiene, contact lenses, chromatography materials, medical equipment, protective topicals, pharmaceutical and especially dermatological formulations, lacquers, coatings, polymers, and plastics. Additional exemplary applications include, but are not limited to, adhesives and sealants, antimicrobial cleansers, soaps, disinfectants, anti-fouling and antimicrobial paints for inside and outside use, antifoulant marine coatings, animal husbandry, antimicrobial wallpapers, antimicrobial dressings and plasters, prostheses and bone cement with antimicrobial activity, dental fillings, dental prostheses, formulations against gastrointestinal infections, active coal, antimicrobial cat litter, air conditioning (e.g., filters and ducts), air inflated construction (e.g., air halls), agricultural and mulch films, all purpose adhesives, appliances and equipment, appliance adhesives and sealants, aprons, artificial leather, artificial plants, artificial wood, and plastic lumber, Astroturf, automobile parts, automotive and truck upholstery, awnings, bags, bandages, barrier fabrics, bathroom accessories, bathtubs, bathtub cement, bedding, beverage dispensers, bibs, boats, boat covers, book covers, bottles, brush bristles, brush handles, brooms, building components (e.g., walls, wallboard, floors, concrete, siding, roofing, shingles, hardware, carpet cleaner, ceilings and commercial and industrial applications), cable sheathing, caps (e.g., hats), cardboard, carpet and carpet underlay, caster wheels, cat litter, clinical thermometers, coats, compact discs, convertible tops, cookware, coolers, cooling towers, cooling water, counter and table tops, conveyor belts, countertops, credit cards, crates (for both food and non-food uses), cups, currency, curtains, cushion pads, cutting boards, decking, dishes, dish cloths, dishwasher components, diving equipment or snorkels, drainage sewer pipe, draperies, dry-film paints, exercise equipment, equipment for slaughterhouses or creameries or diaries, equipment for gyms, saunas or massages, fan blades, fiberfill, filters, fittings, fences, floor coverings, floor and carpet baking, flooring, foam (e.g., for cushions and mattresses), food preparation appliances, food and beverage processing equipment, food and drink containers, storage and bags, food handling equipment, food packaging, food and meat crates, food trays and covers, food wrap, footwear (including, for example, boots, sports equipment, and tools), fruit and vegetable brushes, fruit crates, furniture, garbage bags, garbage cans, garment bags, gaskets, general purpose containers, gloves, gowns (e.g., medical and consumer), grease traps, rigid greenhouses, greenhouse films, grout and joint compound, heating, ventilation and air conditioning, hospital surface and medical instrument disinfection, hoses, ice-making equipment and trays, in-can paints, incontinence care products, indoor and outdoor furniture, industrial equipment, inflatable bed, insulation for wire and cable, insulators, intimate apparel, jacket liners, janitorial equipment, kitchen and bathroom hardware, kitchen sinks and fixtures, kitchen towels, laminate and tile adhesives, laying batteries, life vests, liners, mats, mattress cover pads and filing, mattress adhesives, medical and dental apparel, metal working fluids, mineral slurries, mobile homes, mobile toilets, mops, money, natural and synthetic fibers and fabrics, non-woven fabrics, oilfield, outerwear, packaging, pallets, paper products (e.g., wipes, tissues, wall coverings, towels, book covers, mulch), pillow covers, pipes, pipe sealant and insulating materials, plaster, plastics, plastic films, plates and utensils, playground equipment, plumbing supplies and fixtures (including, for example, toilet bowl seats), plumbing adhesives and sealants, pool liners, process vessels, protective covers, recreational water, resins, refrigerator components, roofing sheets, membranes, shingles and flashing, ropes, rugs, sales counter, sails, sanitary pipes, sealers, sealing compounds for bathrooms, kitchens or glass, sheets and blankets, shoes, shoe insoles, shower curtains, shower tubs, siding for housing, silage wrap, silos, sinks, siphons, skylights, sleeping bags, sleepwear, socks and hosiery, sponges, sprinkler, sportswear and sports equipment, storage containers, stucco, sun roof, sun shades, synthetic latex polymers, napkins, tanks, tape, tarps, telephone boxes or public phones, tents and other outdoor equipment, ticking (e.g., for mattress pillows), tiles, tile grout, toothbrush handle and bristles, toilet paper and handkerchiefs, toilet blocks and cleaners, towels, toothbrush tumbler, toys, trim for outerwear and garments, trunk liners, tubing, umbrellas, uniforms, undergarments, upholstery, vacuum cleaner bags, wall and floor covering, wallpaper, waste bags, water tanks, waste containers, water treatment, water and ice handling equipment and filters, wet suits, wipes, wire and cable, wood, and wood filled plastics.

In certain application areas, enhanced biocidal or antimicrobial activity may be useful in several stages of processing. In one embodiment, plastics and/or polymers comprising cationically modified, mineral-based fillers according to the present invention can be stored in the form of Masterbatches for a period of time, without substantial risk of contamination of the Masterbatch with microorganisms. The skilled artisan recognizes that such a Masterbatch can be processed in the same way as known Masterbatches, or in processing methods hereafter discovered. The treated Masterbatches may be useful in, for example, building and construction, household, items and furnishings, electrical and electronics parts, apparel, textiles and fabrics, coatings and laminates, transportation and recreation, adhesives, sealants and grouts, food contact items and water contact items (e.g., plastic bottles and bottle caps), films, coextrusion films, and exterior and interior automotive parts.

In another embodiment, exemplary plastics and polymers from which the articles may be fabricated comprising at least one cationically modified, mineral-based filler according to the present invention include synthetic, natural, and semisynthetic organic polymers. Examples of polymers include, but are not limited to: aliphatic and aromatic polyesters, such as polyethylene terephthalate, polybutylene terephthalate, polyethylene isophthalate, polyhexamethylene terephthalate, polylactic acid, polyglycolic acid, and liquid crystalline polymers for high performance resins and fibers; polyester block copolymers; aliphatic and aromatic polyamides, such as nylon 6, nylon 66, nylon 610, nylon 11, nylon 12, nylon 1212, poly-p-phenylene terephthalamide, poly-m-phenylene isophthalamide; copolymerised polyamides; polyolefins such as polyethylene, polypropylene, and copolymers thereof; vinyl polymers such as polystyrene, polyacrylonitrile, polyvinylalcohol, polyvinyl acetate, polyvinylchloride, polyvinylidene chloride, ABS resins, and acrylic resins; copolymers of ethylene and vinyl acetate; fluorocarbon polymers such as polytetrafluoroethylene, polyvinylidene fluoride and polyvinyl fluoride; polyurethanes; segmented polyurethane elastomers, spandex or elastane elastomers; polyethers such as polyacetals; polyketones such as polyetherether ketone (PEEK) and polyether ketoneketone (PEKK); polyether and polyester block polymers; polysulfides; polysulfones: polysiloxanes such as polydimethyl siloxane; polycarbonates; thermosetting synthetic polymers such as phenol-formaldehyde copolymer, polyurethane, polyesterurethane, polyetherurethane, polyetherurethaneurea, and polyesterurethaneurea; natural polymers such as cellulosics, cotton and wool; and, regenerated or semi-synthetic polymers such as rayon, cuprammonium rayon, acetate rayon, triacetate rayon, reconstituted silk and polysaccharides. Copolymers, terpolymers, and blends of the polymer species listed are also contemplated.

Enhanced Antimicrobial Activity

The modified mineral-based fillers of the present invention may retain larger quantities of the at least one active ingredient, which may in turn enhance the at least one antimicrobial activity of those materials. In one embodiment, improved antimicrobial activity is determined by measuring the migration rate of silver from the modified mineral-based filler. In another embodiment, the improved antimicrobial activity is determined by measuring the concentration, in parts per million ("ppm"), of metal ions extracted through treatment with a solution of about 0.5 M sulfuric acid.

For the inventions disclosed herein, a lower migration rate or a lower concentration of extracted ions generally shows that the modified mineral-based fillers retain larger quantities of the at least one active ingredient compared to mineral-based fillers that were not subjected to at least one modification process and/or at least one thermal treatment. The lower migration rate or lower concentration of extracted ions may reveal increased levels of at least one antimicrobial activity in the modified mineral-based fillers.

Unless otherwise indicated to the contrary, all numbers expressing quantities of ingredients, reaction conditions, and so forth used in the specification, including claims, are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements. The section headings used in this disclosure are provided merely for the convenience of the reader and are not intended to limit the scope of the inventions described herein.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

By way of non-limiting illustration, examples of certain embodiments of the present disclosure are given below.

EXAMPLES

A natural diatomaceous earth, CelTiX™, was ion-exchanged with silver metal ions at four different ion-exchanged and/or surface retained final silver contents in the filler (i.e., 50 ppm, 100 ppm, 280 ppm, and 25,500 ppm ("2.55%")) for comparison to the original CelTiX™ diatomaceous earth product, which does not contain any measurable silver.

The cation exchange capacity of CelTiX™ was measured at about 22.9 equ/100g, or about 0.23 mmole/g, as determined by sodium-ammonium replacement method. This involved saturating of the exchangeable cation sites with sodium ions first, after washing with alcohol (e.g., isopropanol), and then the filler was ion-exchanged again, this time with ammonium ions. The replaced sodium ions in solution were then determined by inductively coupled plasma (ICP) spectrometric method.

Next, a solution of a silver nitrate was made with water, then a dosage of a CelTiX™ was mixed into the solution. After stirring the slurry for at least 30 minutes, the slurry was filtered. The cake was then dried and redispersed. The retained silver content in the cationically modified filler was then analyzed with a ThermoARL Advant'XP wavelength dispersive X-ray fluorescence (WDXRF).

After ion-exchange, a portion of each sample was calcined at 800° C., such that no measurable crystalline silica formed. The calcinations were carried out with a Linberg HEVI DUTY laboratory muffle furnace. The samples were calcined at 800° C. for different durations. The crystalline silica contents in the calcined samples were monitored with a PANalytical X'pert X-ray Diffractometer (XRD). The XRD method used for crystalline silica analysis had a quantitative detection limit (QDL) of 0.2% by weight. Calcinations at this temperature (i.e., <800° C.) generally do not form crystalline silica, and the elemental compositions remain the same as the uncalcined feeds.

The four samples of calcined, Ag-doped CelTiX™, along with the untreated CelTiX™, were analyzed by WDXRF for their bulk compositions, as shown in Table 1.

TABLE 1

| Components | Original CelTiX ™ (untreated) | CelTiX ™- 50 ppm Ag | CelTiX ™- 100 ppm Ag | CelTiX ™- 280 ppm Ag | CelTiX ™- 2.55% Ag |
|---|---|---|---|---|---|
| $SiO_2$ (%) | 94.70 | 94.75 | 94.73 | 94.85 | 91.60 |
| $Al_2O_3$ (%) | 2.55 | 2.60 | 2.58 | 2.58 | 2.56 |
| $Fe_2O_3$ (%) | 0.77 | 0.78 | 0.79 | 0.76 | 0.90 |
| CaO (%) | 0.67 | 0.68 | 0.69 | 0.64 | 1.19 |
| $Na_2O$ (%) | 0.42 | 0.41 | 0.41 | 0.40 | 0.13 |
| MgO (%) | 0.41 | 0.37 | 0.38 | 0.36 | 0.35 |
| $K_2O$ (%) | 0.14 | 0.14 | 0.14 | 0.13 | 0.19 |
| Ag (ppm) | Not Detected | 50 | 100 | 280 | 25500 |
| Total (%) | 99.66 | 99.72 | 99.72 | 99.74 | 99.47 |

Table 1 indicates that by changing the concentrations of silver nitrate in the solution and/or the dosage of fillers to be treated, the final levels of silver concentration in the fillers can be controlled, which may be less than about 20 ppm, and may reach or even exceed the theoretical cation exchange capacity. This may allow for control of the active ingredient levels in a filler, and different levels of active ingredients may be used in different applications.

A portion of each sample which were calcined at 800° C. for 30 minutes was then placed in a 0.5 M sulfuric acid solution for four hours at room temperature, and the concentration of silver that leached from each sample was measured by an ICP spectrometric method, as shown below in Table 2.

TABLE 2

| Sample ID | Sample Loading in Solution (g/100 ml) | Ag Leached from Unheated Filler (ppm) | Ag leached from Calcined Filler* (ppm) |
|---|---|---|---|
| CelTiX ™-50 ppm Ag | 0.5 | 0.4 | 0 |
| CelTiX ™-100 ppm Ag | 0.5 | 0.5 | 0 |
| CelTiX ™-280 ppm Ag | 0.5 | 1.1 | 0 |
| CelTiX ™-2.55% Ag | 0.5 | 136 | 17 |

*The fillers were calcined at 800° C. for 30 minutes.

Table 2 reveals that, for each one of the samples tested, the calcined, Ag-treated filler retained greater amounts of Ag metal ions than un-calcined, Ag-treated filler, and that little or no leachable silver from calcined fillers were detected. This indicates that the silver ions have been affixed onto the fillers, and they can even survive the leaching of a strong acid solution.

A further portion of three of the four samples were placed in deionized water for four hours at room temperature and the concentration of silver that leached from each sample was measured by the same ICP method, as shown below in Table 3.

TABLE 3

| Sample ID | Sample Loading in Solution (g/100 ml) | Ag Leached from Unheated Filler (ppm) | Ag leached from Calcined Filler* (ppm) |
|---|---|---|---|
| CelTiX ™-50 ppm Ag | 0.5 | 0.06 | 0 |
| CelTiX ™-280 ppm Ag | 0.5 | 0.2 | 0 |
| CelTiX ™-2.55% Ag | 0.5 | 57.4 | 0.7 |

*The fillers were calcined at 800° C. for 30 minutes

Table 3 again reveals that, for each one of the samples tested, the calcined, Ag-treated filler retains greater amounts of Ag metal ions than un-calcined, Ag-treated filler.

A further portion of three of the four samples were placed in deionized water for 24 days at room temperature and the concentration of silver that leached from each sample was measured by the same ICP method, as shown below in Table 4.

TABLE 4

| Sample ID | Sample Loading in Solution (g/100 ml) | Ag Leached from Unheated Filler (ppm) | Ag leached from Calcined Filler* (ppm) |
|---|---|---|---|
| CelTiX ™-100 ppm Ag | 0.5 | 0.02 | 0 |
| CelTiX ™-280 ppm Ag | 0.5 | 0.2 | 0 |
| CelTiX ™-2.55% Ag | 0.5 | 52.4 | 2.5 |

*The fillers were calcined at 800° C. for 30 minutes

Table 4 reveals that, for each one of the samples tested, the calcined, Ag-treated filler retains greater amounts of Ag metal ions than un-calcined, Ag-treated filler.

What is claimed is:

1. A method comprising:
    subjecting particles of at least one mineral-based filler comprising diatomaceous earth to cationic modification with at least one active ingredient comprising silver oxide to form a modified mineral-based filler;
    subjecting the modified mineral-based filler to calcination at a temperature between about 427° C. and about 900° C., and
    adding the modified mineral-based filler to a synthetic, natural, or semisynthetic organic polymer to form a polymer composition or resin;
    wherein the average diameter of the particles of the mineral-based filler ranges from 1 micron to 10 microns.

2. The method of claim 1, further comprising adding the polymer composition or resin to a resin, a biocidal polymer, an article of clothing, a lacquer coating, a paint, a cosmetic formula, a personal hygiene product, a work hygiene product, a chromatography material, medical equipment, surgical equipment, a protective topical, a pharmaceutical formulation, a dermatological formulation, or a plastic.

3. The method of claim 1, wherein the average diameter of particles of the mineral-based filler ranges from 1 micron to 5 microns.

4. The method of claim 1, wherein the at least one active ingredient further comprises at least one biocide, antibiotic, fungicide, mildewcide, preservative, or antimicrobial agent.

* * * * *